United States Patent [19]

Azria et al.

[11] Patent Number: 5,561,149
[45] Date of Patent: Oct. 1, 1996

[54] USE OF CERTAIN IMIDAZOL CARBAZOLS IN TREATING STRESS-RELATED MANIC-DEPRESSIVE DISORDERS

[75] Inventors: Moise Azria, Basel, Switzerland; Karl-Heinz Buchheit, Lörrach, Germany; Keith A. Dixon, Neuenegg, Switzerland; Günther Engel, Weil am Rhein, Germany; Rudolf K. A. Giger, Muttenz, Switzerland

[73] Assignee: Sandoz Ltd., Basel, Switzerland

[21] Appl. No.: 403,620

[22] Filed: Mar. 14, 1995

Related U.S. Application Data

[63] Continuation of Ser. No. 111,805, Aug. 25, 1993, abandoned, which is a continuation of Ser. No. 3,926, Jan. 13, 1993, abandoned, which is a continuation of Ser. No. 890,493, May 28, 1992, abandoned, which is a continuation of Ser. No. 701,934, May 17, 1991, abandoned, which is a continuation of Ser. No. 423,916, Oct. 19, 1989, abandoned, which is a continuation of Ser. No. 78,336, Jul. 27, 1987, abandoned.

[30] Foreign Application Priority Data

Jul. 30, 1986 [GB] United Kingdom .................. 8618614
Aug. 7, 1986 [DE] Germany .......................... 36 26 703.1

[51] Int. Cl.$^6$ ................................................. A61K 31/415
[52] U.S. Cl. ................................................................. 514/397
[58] Field of Search ..................................... 514/304, 397

[56] References Cited

U.S. PATENT DOCUMENTS

| 4,721,720 | 1/1988 | Wootton et al. | 514/214 |
| 4,789,673 | 12/1988 | Donatsch et al. | 514/304 |
| 4,883,803 | 11/1989 | Tyers | 514/304 |

OTHER PUBLICATIONS

Br. J. Pharmacol. Abstract No. C111, 90:88P (Dec. 17th–19th, 1986).

*Primary Examiner*—Raymond Henley, III
*Attorney, Agent, or Firm*—Robert S. Honor; Melvyn M. Kassenoff; Joseph J. Borovian

[57] ABSTRACT

Use of a mono or bicyclic carbocyclic, or heterocyclic carboxylic, acid ester or amide or an imidazolyl carbazol in the manufaccure of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

2 Claims, No Drawings

USE OF CERTAIN IMIDAZOL CARBAZOLS IN TREATING STRESS-RELATED MANIC-DEPRESSIVE DISORDERS

This is a continuation of application Ser. No. 08/111,805, filed Aug. 25, 1993, now abandoned, which in turn is a continuation of application Ser. No. 08/003,926, filed Jan. 13, 1993, now abandoned, which in turn is a continuation of application Ser. No. 07/890,493, filed May 28, 1992, now abandoned, which in turn is a continuation of application Ser. No. 07/701,934, filed May 17, 1991, now abandoned, which in turn is a continuation of application Ser. No. 07/423,916, filed Oct. 19, 1989, now abandoned, which in turn is a continuation of application Ser. No. 07/078,336, filed Jul. 27, 1987, now abandoned.

This invention relates to new uses and modes of administration of serotonin $5HT_3$ antagonists and also to mono- or bicyclic carbocyclic, or heterocyclic carboxylic, acid ester and amides and imidazolyl carbazols, e g., imidazolylmethylcarbazols.

The compounds may be used in any pharmaceutically acceptable form, including the free base and at least for the esters and amides, in acid addition and quaternary ammonium salt forms.

These compounds are referred to hereinafter as compounds of the invention.

The above mentioned esters, and amides and imidazolyl carbazols have in general serotonin $5HT_3$ antagonist activity which may have not been previously recognized. These esters, amides and carbazols are in general known for example from Belgian patents 897117, 900425 and 901274. These compounds are described therein as being serotonin $5HT_3$ receptor antagonists or serotonin M receptor antagonists (serotonin M receptors have been reclassified as $5HT_3$ receptors).

The compounds are for treatment as anti-migraine agents, anti-arrhythmics, and for treatment of serotonin-induced gastro-intestinal disorders including emesis, e.g. induced by anti-cancer agents.

Other classes of the compounds of the invention are known from e.g. European patent publications 13138A, 250444A, and 214772A and British Patent publication 2153821A.

We have now discovered that these compounds have interesting new uses and modes of administration which have been hitherto unrecognized.

In a first aspect the present invention provides use of a mono- or bicyclic carbocyclic, or cyclic heterocyclic carboxylic acid ester or amide e.g. of a cyclic alcohol or amine, containing nitrogen as a ring atom, or a serotonin $5HT_3$ antagonist or an imidazolyl carbazol, for the treatment of stress-related psychiatric disorders, rhinitis, or serotonin-induced nasal disorders or lung embolism, or coadministration with another active agent to increase the bioavailability thereof, or for nasal administration or for the manufacture of a medicament suitable therefor. The invention also provides a method of treating a subject with any of the indications which comprises administering to a subject in need of such treatment a compound of the invention.

The invention also provides:

i) a process for the production of a pharmaceutical composition adapted for the treatment of stress-related psychiatric disorders, forincreasing viligance, for the treatment of rhinitis, or for serotonin-induced nasal disorders or lung embolism which comprises working up a compound of the invention with pharmaceutical carriers and diluents to manufacture unit dosage formulations for said indications.

ii) A process for the production of a nasal composition which comprises working up a compound of the invention with an appropriate nasal carrier, and optionally incorporating a surface active agent and optionally filling the resultant composition into a nasal applicator.

iii) A process for the production of a pharmaceutical composition having improved bioavailability which comprises working up a compound of the invention, e.g. a compound of formula I or Ia as defined hereinafter, with another active agent, e.g. a peptide, and if desired formulating as a unit dosage form.

In a group of compounds the ester or amide is an ester or amide of a cyclic alcohol, or amine, containing nitrogen as a ring atom.

In a sub-group of compounds the heterocycle is a bicyclic heterocycle preferably aromatic.

In another group of compounds the ester or amide or serotonin $HT_3$ antagonist is a dicarboxyclic or heterocyclic carboxylic acid ester, or carboxylic acid amide, of a piperidinol containing an alkylene bridge, or of piperidylamine containing an alkylene bridge, or of an ester, or amide, of a substituted benzoic acid, or of a piperidinol or piperidylamine containing an alkylene bridge, with the proviso that in each benzoic acid amide the alkylene bridge of the piperidyl ring is bonded to the nitrogen atom and to a cyclic carbon atom.

In another group of compounds the ester or amide or serotonin $5HT_3$ antagonist or imidazolcarbazol is a compound of formula I
Wherein A is

 (I)

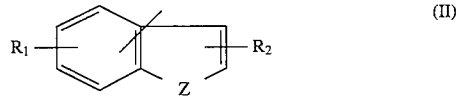 (II)

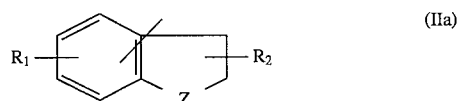 (IIa)

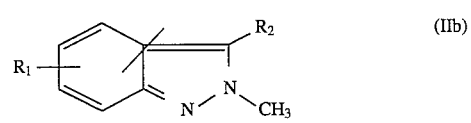 (IIb)

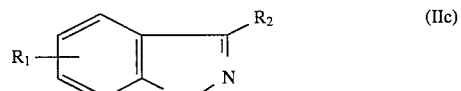 (IIc)

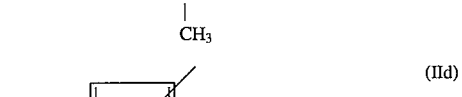 (IId)

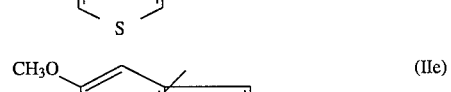 (IIe)

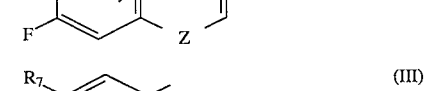 (III)

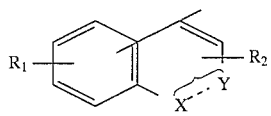 (IV)

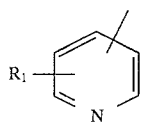 (V)

wherein the free valence is attached to either fused ring in formula II, IIa, IIb, IIe or IV, X—Y is —CH=CH—, —O—CH$_2$— or —N=CH—, Z is —CH$_2$—, —NR$_3$—, —O— or —S—, R$_1$ and R$_2$ are independently hydrogen, halogen, (C$_{1-4}$)alkyl, (C$_{1-4}$)alkoxy, hydroxy, amino, (C$_{1-4}$)alkylamino, di(C$_{1-4}$)alkylamino, mercapto or (C$_{1-4}$)alkylthio, R$_3$ is hydrogen, (C$_{1-4}$)alkyl, acyl, (C$_{3-5}$)alkenyl, aryl or arylalkyl, and R$_4$ to R$_7$ are, independently, hydrogen, amino, nitro, (C$_{1-4}$)alkylamino, di(C1,4)alkylamino, halogen, (C$_{1-4}$)alkoxy, (C$_{1-4}$)alkyl, (C$_{1-4}$)alkanoylamino, pyrrolyl, sulfamoyl, or carbamoyl, B is —CO— or —SO$_2$—, C is —O— or —NH—, a bond, D is a group of formula

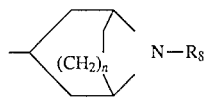 (VI)

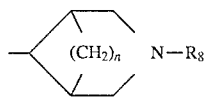 (VII)

wherein n is Z, 3 or 4

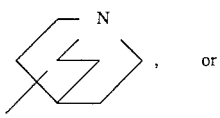 (VIII)

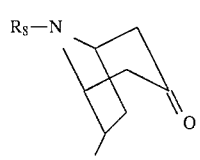 (IX)

wherein R$_8$ is hydrogen, (C$_{1-7}$)alkyl, (C$_{3-5}$)alkenyl or aralkyl, and in formula VIII the bond is in position 3 or 4, when B is CO, additionally D may be a group of formula

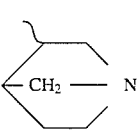 (X)

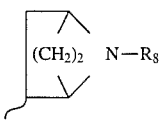 (XI)

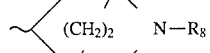 (XII)

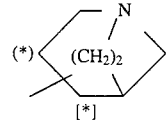 (XIII)

wherein t is 1 or 2, and R$_8$ is as defined above,

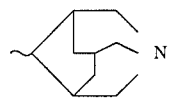 (XIV)

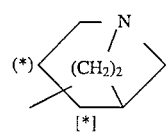 (XV)

wherein the bond is in the position 3 (*) or 4 [*],

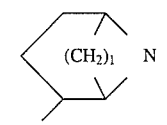 (XVI)

wherein l is 2 or 3,

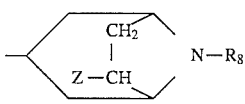 (XVII)

where Z is (C$_{1-4}$)alkoxy,

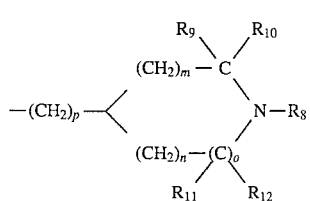 (XVIII)

wherein R$_9$ to R$_{12}$ are independently hydrogen or (C$_{1-4}$)-alkyl and m is 0, 1 or 2 and n, o, p independently are 0 or 1,

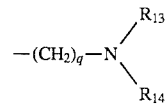 (XIX)

wherein q is 2 or 3, and R$_{13}$ and R$_{14}$ independently are (C$_{1-4}$)alkyl,

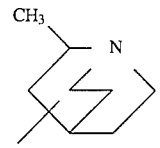 (XX)

wherein the bond is in position 3 or 4,

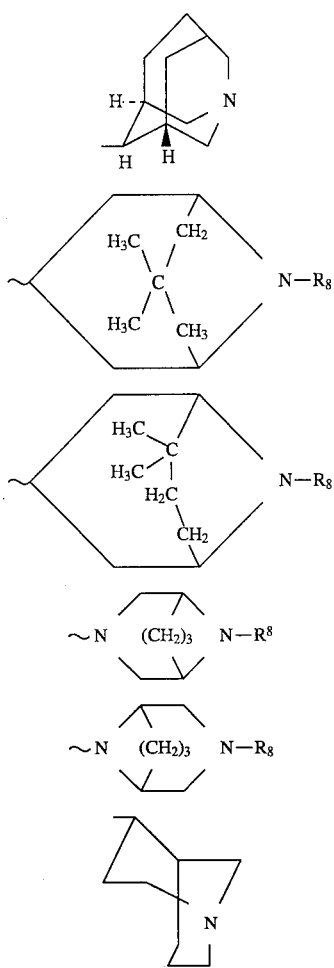

and $R_8$ is as defined above, in free base form, acid addition salt form or quaternary ammonium salt form, or a compound of formula Ia

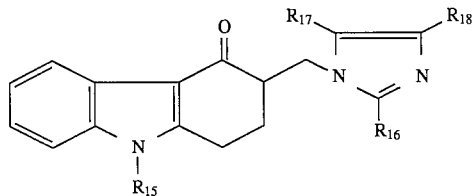

wherein $R_{15}$ is hydrogen, $(C_{1-10})$alkyl, $(C_{3-9})$cycloalkyl, $(C_{3-6})$alkenyl, phenyl or phenyl $(C_{1-3})$alkyl and one of the groups $R_{16}$, $R_{17}$ and $R_{18}$ is hydrogen, $(C_{1-6})$alkyl, $(C_{3-7})$cycloalkyl, $(C_{2-6})$alkenyl or phenyl $(C_{1-3})$alkyl and the others independently are hydrogen or $(C_{1-4})$alkyl.

In a sub-group the compound is of formula I wherein A is chosen from formula II, III, IV and V, $R_3$ is other than acyl, C is —O— or —NH— and D is chosen from formula VI to XVIII, with the proviso that, when A is formula III, B is CO and C is NH, D is not a group of formula VI, in free base form, in acid addition salt form or in quaternary ammonium salt form.

In a further group of compounds of formula I' A is a group of formula II'

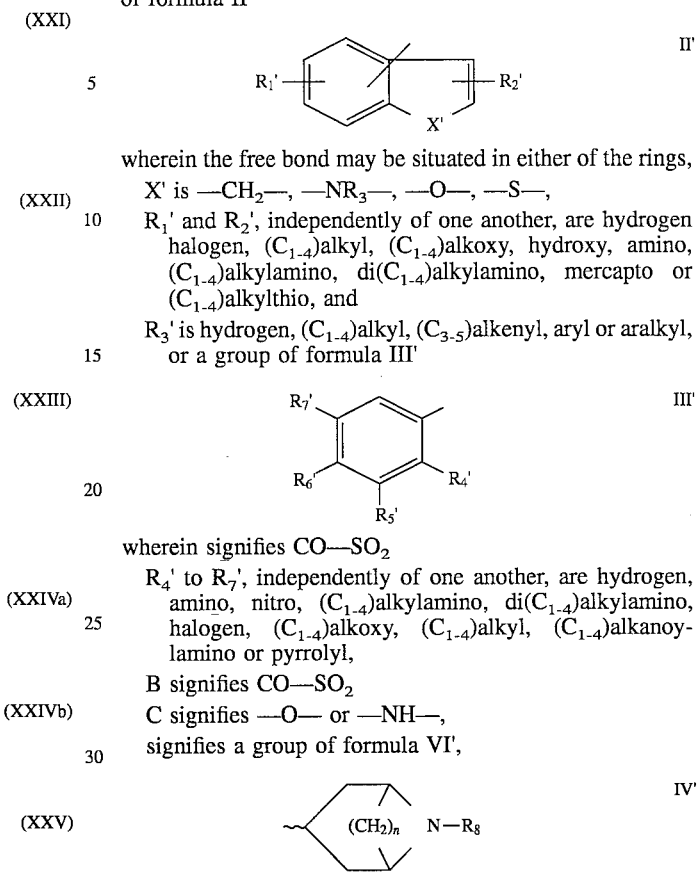

wherein the free bond may be situated in either of the rings,

X' is —$CH_2$—, —$NR_3$—, —O—, —S—, $R_1'$ and $R_2'$, independently of one another, are hydrogen halogen, $(C_{1-4})$alkyl, $(C_{1-4})$alkoxy, hydroxy, amino, $(C_{1-4})$alkylamino, di$(C_{1-4})$alkylamino, mercapto or $(C_{1-4})$alkylthio, and $R_3'$ is hydrogen, $(C_{1-4})$alkyl, $(C_{3-5})$alkenyl, aryl or aralkyl, or a group of formula III'

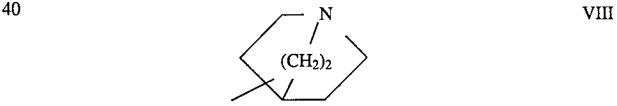

wherein signifies CO—$SO_2$ $R_4'$ to $R_7'$, independently of one another, are hydrogen, amino, nitro, $(C_{1-4})$alkylamino, di$(C_{1-4})$alkylamino, halogen, $(C_{1-4})$alkoxy, $(C_{1-4})$alkyl, $(C_{1-4})$alkanoylamino or pyrrolyl, B signifies CO—$SO_2$ C signifies —O— or —NH—, signifies a group of formula VI',

IV' wherein n is 2, 3 or 4 and $R_8'$ is hydrogen, $(C_{1-7})$alkyl, $(C_{3-5})$alkenyl or aralkyl, or a group of formula VIII,

VIII with the proviso that when A is a group of formula III and B is —NH—, then D signifies a group of formula VIII.

A further group comprises formula I wherein A is a group of formula II or III wherein B═—CO—, C═—O— or —NH— then D is a group of a group of formula VII, IX, X, XI or one of XIII to XXV or A is group of formula IIa, IIb, IIc, IId, IIe, IV or V and B, C and D are as defined above.

Another group of compounds of formula I comprises compounds wherein A is formula II or III, wherein $R_4$ to $R_7$ are other than sulfamoyl or carbamoyl, D is VI or VIII with the proviso when A is III and C is —NH— and D is VIII.

Preferred compounds include:

Indole-3-yl-carboxylic acid endo-8-methyl-8-aza-bicyclo 3,2,1]oct-3-yl ester, (hereinafter compound E) benzo[b]thiophen-3-ylcarboxylic acid endo-9-methyl-9-aza-bicylo[3,3,1]-non-3-yl ester, 5-fluoro-1-methyl-indol-3-yl carboxylic acid endo-9-methyl-9-aza-bicyclo[3,3,1]-non-3-yl ester, 1,2,3,9-tetrahydro-9-methyl-3-[(2-methyl-1H-imidazol-1-yl)methyl-4H-carbazol-4-one (hereinafter compound H) and in free base form or in acid addition salt form 1-methyl-indazol-3-yl carboxylic acid 9-methyl-9-aza-bicyclo[3,3,1]non-3α-yl-amide.

In one group of compound the compounds of formula I is a group of formula II, in particular Z is $NR_3$, O, or S.

In another group the compound of formula I is a group of formula III. In a sub-group D is VI. In a 2nd sub-group D is VII. In a 3rd sub-group D is VIII. In a 4th sub-group D is IX. In a 5th sub-group D is X. In a 6th sub-group D is XI. In a 7th sub-group D is XII. In a 8th sub-group D is XIII. In a 9th sub-group D is XIV. In a 10th sub-group D is XV. In a 11th sub-group D is XVI. In a 12th sub-group D is XVII. In a 13th sub-group D is XVIII.

Preferably D is VI or VIII.

A preferred group of compounds comprises a compound wherein A is a group of formula II wherein $R_1$ and $R_2$ are independently hydrogen, halogen, $(C_{1-4})$alkyl or alkoxy; $R_1$ is in position 4 or 5;

$R_3$ is hydrogen, acetyl or $(C_{1-4})$alkyl and the corresponding bond is in position 3, 4 or 5, The present invention also provides novel compounds of formula Ib A'—CO—C'—D'  Ib wherein 1) A' is a group of formula II, wherein $R_1$, $R_2$ and Z are as defined above, C' is —O— or —NH— and D' is a group of formula XIX, wherein q, $R_{13}$ and $R_{14}$ are as defined above, 2) A' is a group of formula III, wherein $R_4$ and $R_6$ are each hydrogen, and $R_5$ and $R_7$ are each chlorine, C' is —O— and D' is one of the groups of formula VI, wherein n is 3 and $R_8$ is as defined above or VIII, 3) A' is a group of formula II, wherein $R_1$, $R_2$ and Z are each as defined above, C' is —O— and D' is a group of formula XX, wherein the bond is in position 3 or 4, 4) A' is a group of formula IIa, wherein $R_1$, $R_2$ and Z are as defined above, C' is —NH— or —$CH_2$— and D' is a group of formula VI, wherein $R_8$ is as defined above or VIII, wherein the bond is in position 3 or 4, 5) A' is a group of formula IIb, wherein $R_1$, $R_2$ and Z are as defined above, C' is —O— and D' is a group of formula VI, wherein $R_8$ is as defined above, 6) A' is a group of formula IIc, wherein $R_1$, $R_2$ and Z are as defined above, C' is —O— and D' is a group of formula VI, wherein $R_8$, is as defined above, 7) A' is a group of formula IId, C' is —O— and D' is a group of formula VI, 8) A' is a group of formula II, wherein $R_1$, $R_2$ and Z are as defined above, C' is —$NCH_3$—, and D' is a group of formula VI, wherein $R_8$ is as defined above, 9) A' is a group of formula II, wherein $R_1$, $R_2$ and Z are as defined above, C' is —O— and D' is a group of formula XXI, 10) A' is a group of formula III, wherein $R_4$–$R_7$ are as defined above, C' is —NH— and D' is a group of formula XXII, wherein $R_8$ is as defined above, 11) A' is a group of formula II, wherein $R_1$ is 6-hydroxy- or 6-methoxy- or 5-methyl, $R_2$ is hydrogen and Z is —NH—, C' is —O— and D a group of formula VI, wherein $R_8$ is as defined above, 12) A' in a group of formula II, wherein $R_1$, $R_2$ and Z are as defined above, C' is a bond and D' is a group of formula VI, wherein $R_8$ is as defined above, 13) A' is a group of formula II, wherein $R_1$, $R_2$ and Z are as defined above, C' is —O— and D' is a group of formula XXIII, wherein $R_8$ is as defined above, 14) A' is a group of formula II, wherein $R_1$, $R_2$ and Z are as defined above, C' is —O— and D' is a group of formula XXII, wherein $R_8$ is as defined above, 15) A' is a group of formula IIe, wherein Z is as defined above, C' is —O— and D' is a group of formula VI, wherein $R_8$ is a defined above, 16) A' is a group of formula II, wherein $R_1$, $R_2$ and Z are as defined above, C' is a bond and D' is a group of formula XXIVa, wherein $R_8$ is as defined above, 17) A' is a group of formula II, wherein $R_1$, $R_2$ and Z are as defined above, C' is a bond and D' is a group of formula XXIVb, wherein $R_8$ is as defined above, 18) A' is a group of formula II, wherein $R_1$ and $R_2$ are as defined above, Z is N-acyl, C' is —O— and D' is a group of formula VI, wherein $R_8$ is as defined above, 19) A' is a group of formula II, wherein $R_1$ is hydroxy, $R_2$ is hydrogen and Z is —NH—, C' is —$CH_2$— and D' is a group of formula VI, wherein $R_8$ is as defined above, in free base form or in acid addition salt form or quaternary ammonium salt form.

The present invention also provides a process for the production of a compound of formula Ib as defined above in free base form or in acid addition salt form or in quaternary ammonium salt form, which includes the step of:

a) for the production of a compound of formula Ib wherein C' is —O— or —NH— reacting a compound of formula XXX

A'—COOH  XXX wherein A' is as defined above, or a reactive derivative thereof, or a precursor of the acid or reactive derivative with an appropriate compound of formula XXXI

H—C'—D'  XXXI wherein C' and D' are as defined above, or a precursor of this compound, or b) for the production of a compound of formula Ib wherein C' is —$CH_2$—, reacting a compound of formula XXXII A'—Mg—Hal  XXXII wherein A' is as defined above, and Hal is chlorine, bromine or iodine, with an appropriate compound of formula XXXIII ClOC—$CH_2$—D'  XXXIII, wherein D' is as defined above, in free base or protected form under conditions of a Grignard reaction, and removing any protecting group present c) for the production of a compound of formula Ib wherein C' is a direct bond, reacting a compound of formula XXXII as defined above, with an appropriate compound of formula XXXIV Cl—OC—D'  XXXIV wherein D' is as defined above, under conditions of a Grignard reaction d) for the production of a compound of formula Ib wherein C' is a —$NCH_3$— group, reacting a compound of formula XXX as defined above with an appropriate compound of formula XXXI wherein C' is —$NCH_3$— e) for the production of a compound of formula Ib wherein Z is N-acyl- wherein an appropriate compound of formula I, wherein A is a compound of formula II and Z is —NH—, B is —CO—, C is —O— and D is as defined above is acylated, and recovering the compound of formula Ib in free base form, acid addition salt, form or quaternary ammonium salt form.

The reactions may be effected in conventional manner, e.g. as described in the patent publications referred to above or in analogous manner for known compounds. The processes may be generally effected in an inert solvent at e.g. from about −30° C. to about 200° C. using conventional reagents.

Compounds of formula Ib wherein C' is —O— or —NH— (i.e. groups 1 to 7, 9 to 11, 13 to 15 and 18) are conveniently produced by process a), e.g. as described in Belgian Patent No. 897117.

Compounds of formula Ib wherein C' is —CH$_2$— (i.e. groups 4 and 19) are conveniently produced by process b), e.g. as described in Belgian Patent No. 903,984.

Compounds of formula Ib wherein C' is a direct bond (i.e. groups 12, 16 and 17) may be conveniently produced by process c), e.g. as described in Belgian Patent No. 903,984.

Compounds of formula Ib wherein C' is —NCH$_3$— (i.e. group 8) may be conveniently produced according to process d) which may be effected conveniently as for process a). Starting materials may be conveniently obtained by reacting the corresponding free amine with chloroformic acid ethyl ester and reduction of the product with lithium aluminium hydride.

Compounds of formula Ib wherein Z is N-acyl (i.e. group 18) may be conveniently produced according to process e), in conventional manner e.g. by acylating a compound as disclosed e.g. in Belgian Patent No. 897,117 with an acylating agent such as acetic acid anhydride or benzyl chloride.

The resultant compounds may be converted in conventional manner into acid addition salt form and back into free base forms and also converted in conventional manner into the quaternary ammonium salt form.

Examples of each of these groups are described hereinafter.

The antagonistic action against 5-HT$_3$ receptors of the preferred compound ICS 205-930 (indol-3-yl carboxylic acid endo-8-methyl-8-aza-bicyclo[3.2.1]oct-3-yl ester) on the rabbit vagus, rabbit heart and guinea pig ileum has been described (P. Donatsch et al., Br.j. Pharmacol. 1984, 81,348), and also its topical application to humans as the first 5-HT$_3$ antagonist.

In the Belgian Patent No. 897,117 it was also stated that the compounds disclosed therein are indicated as antipsychotics.

We have now found e.g. from ethological and endocrinological tests that the compounds of the invention are useful for the treatment of stress-related psychiatric disorders, including stress related-social phobias and social withdrawal, affective disorders, psychoses, especially manic depressive disorders and promote approach-oriented behaviour in behaviour perturbed by stress.

The compounds of the invention also increase vigilance, e.g. in geriatrics.

Trials have been carried out on the effects of the compounds of the invention on approach-oriented behaviour in mice. The compounds increase approach-oriented behaviour in stress-situations normally inhibitory to social responses. Thus situations involving unfamiliar surroundings, contact with foreign aggressive opponents, competition for food, were created under reversed lighting conditions whereby observations were performed during the darkphase. Under these conditions, untreated rodents exihibit high levels of flight, particularly depressive ambivalence and escape behaviour, but low levels of social behaviour involving approach activity. Anxiolytics like diazepam reduce the ambivalent behaviour and can increase social behaviour. In food deprived mice under white light, certain antidepressants e.g. bupropion and impramine, but also atypical anxiolytics e.g. bupropion as well as the compounds of the invention, increase approach-oriented social behaviours.

Intruder test

Study A

A foreign male mouse (intruder), placed for 6 minutes, into the cage of an isolated male is attacked and responds with defensive escape patterns collectively known as "flight". Flight and associated defensive activities over-ride the intruder's tendency to approach the attacker so that much of the behaviour includes social forms of ambivalence.

Intruders receiving oral doses of benzodiazepines show less of these defensive activities and more approach-oriented behaviour (A. K. Dixon Triangle 1982, 21, 95–105; M. Krisak, Br. J. Pharmacol 1975, 55, 141–150), e.g. investigation, aggression and sexual activity.

The compounds of the invention are administered 1 hour before the encounter per-orally at from about 0.1 to about 10 mg/kg. Groups of 8 mice pairs are used. The frequency and duration of social and non-social behaviour of the mice were recorded using ethological techniques.

The compounds increase social oriented activity.

In this test compound E at a dose of 1 mg/kg increased the frequency (from ca 60 to 80) and duration of social interaction (from ca 90 to 120 seconds).

Study B

Study A was modified using a large cage (59×38.5×20 cm) which allowed greater freedom of movement so that elements of defense could be separated more clearly from the approach-oriented social activities. The compounds of the invention were given i.p. at doses from about 0.01 to about 100 microgram/kg 45 minutes before the encounter.

Indruders received the drug. It was found that the compounds of the invention clearly promoted the approach-oriented social activities. They also reduced escape behaviour, a special form of flight. In this test at a dose of 1 microgram/kg compound E promoted 8 elements of approach oriented social activities by about 40 per cent. Compound E also reduced escape behaviour. Compound H at the same dose promoted 3 elements of approach-oriented social activities by about 40 per cent. It's effect on escape behaviour was less. It did however increase cage exploratory behaviour indicative of a stimulant effect.

Competitive feeding

Study C

In this test 8 pairs of male OF-1 mice deprived of food for 6 hours are forced to compete over 6 minutes for a single food pellet. Because of the close proximity of the mice the tendency to eat is competitively offset by the tendency to interact socially, One partner receives a compound of the invention at an oral dose from about 0.01 to about 1 mg/kg 1 or 2 hour before the encounter. Frequencies and durations of social activities were recorded for both animals with the aid of a posture and timer machine (K. Hausamann, A. K. Dixon, Physiol. Behav. 1982, 28, 743–745), In this test benzodiazepines increase eating behaviour more than social interactions. Antidepressants may increase such social activities. The compounds of the invention increase approach-oriented social behaviour, more than eating.

Compound E at a dose of 0.1 mg/kg p.o. given 2 hours before the encounter increased, relative to controls, the frequency (54 percent) and duration (321 per cent) of social interactions. In contrast frequency of feeding increased by only 4 per cent and their duration 55 per cent.

Stretched Attend Postures (SAP) (No conflict)

Mice placed upon an unfamiliar elevated platform in a novel environment display characteristic stretched body postures called SAP's which signify amibivalence. Drugs which have putative anxiolytic reactions, e.g. benzodiazepines, barbiturates, and buspirone reduce the incidence of SAP's (H. P. Käsermann, Psychopharmacology 1986, 89, 31–37).

The compounds of the invention administered p.o. at a dose of from about 0.1 to about 10 mg/kg. 2 hours before the test reduce the duration of SAP when placed on the platform for 2 minutes under conditions where no other mice are present.

The durations in the case of compound E at 0.1 mg/kg were similar to that observed with clobazam at the same dose and at higher doses the effect was less.

Corticosterone levels (Endocrinological profile)

Mice subjected to a novel environment. e.g. on transferring them from one room to another via a trolley, exhibit a rise in plasma corticosterone typical of stress related disturbances which are reduced by benzodiazepines and barbiturates (Lahti R. A. Borsulm C., Res. Comm.Chem.Path.Pharm.11: 596–603; G. Le Fur et al., J.Pharm.exp.Ther. 211: 305–308). Reduction is observed with the compounds of the invention at from about 0.1 to 10 mg/kg p.o. compound E reduces such stress-induced corticosterone at about 1 to 10 mg/kg p.o. whilst lower doses from about 0.1 to about 0.3 mg/kg increase basal plasma levels of this hormone. This profile is analogous to that observed with diazepam.

Taken together, the results of these studies also show that compounds of the invention promote approach-oriented social behaviour in stressful situations. This suggests that the compounds of the invention are of use in stress-related psychiatric disorders, e.g. where the treatment of social withdrawal, affective disorders, and other stress-related illnesses is desired.

The increases in corticosterone also suggest that compounds of invention increase vigilance, thus indicating a potential use for the compounds in disorders of vigilance e.g. geriatric illnesses.

The compounds of the invention may be administered in similar manner to known standards, e.g. bupropion. The preferred compound E and bupropion have been found to have a pronounced effect on promoting social interaction under stress related conditions. For example, compound E increased the mean frequency of social interactions in the competitive feeding experiment study c) by 54 per cent at 0.01 mg/kg compared to bupropion provoking an increase of 179 per cent at 2.5 mg/kg. It is indicated that compound E will be useful in the treatment of stress-related psychiatric disorders at a daily oral dose of from 0.1 mg which could be increased up to 50 mg.

Compounds of the invention including and excluding (i) compounds of formula I wherein A is a group of formula II or III, B is CO, C is —O— or —NH— and D is a group of formula VI, VIII and XII and (ii) compounds of formula Ib also have an anxiolytic effect which more general indication is also indicated by the above testing.

The use of the compounds of formula I wherein (i) A is a group of formula II or III and B is —CO—, C is —O— or —NH— and D is a group of formula VII, IX, X, XI and one of XIII to XXV, and (ii) A is a group of formula IIa, IIb, IIc, IId, IIe, IV or V as an anxiolytic or in the manufacture of a medicament available therefor also forms part of the present invention and is also shown by the above testing.

For these indications, the appropriate dosage will, of course, vary depending upon, for example, the compound employed, the host, the mode of administration and the nature and severity of the condition being treated. However, in general, satisfactory results are indicated to be obtained at daily dosages from about 0.001 mg/kg to about 50 mg/kg animal body weight. In humans, an indicated daily dosage is in the range from about 0.1 mg to about 50 mg of a compound of the invention conveniently administered, for example, in divided doses up to four times a day.

In a further aspect the present invention provides use of a mono or bicyclic carbocyclic or heterocyclic carboxylic acid esters or amides of a cyclic alcohol or amine containing nitrogen as a ring atom in free base form or in acid addition salt or quaternary ammonium salt form as $5\text{-HT}_3$ antagonists in the manufacture of a medicament suitable for the treatment of serotonin induced psychiatric disorders, e.g. when chosen from one of the following: anxiety, social withdrawal, affective disorders, psychoses and other stress-related illnesses i.e., disorders of vigilance, e.g. geriatric illnesses Preferred compounds include:

Indol-3-yl carboxylic acid endo-8-methyl-8-aza-bicyclo[3.2.1]oct-3-yl ester [hereinafter compound E].[ICS]

Benzo[b]thiophen-3-yl carboxylic acid endo-9-methyl-aza-bicyclo[3.3.1]non-3-yl ester [hereinafter compound F].

5-fluoro-1-methyl-indol-3-yl carboxylic acid endo-9-methyl-9-aza-bicylco[3,3,1]non-3-yl ester [hereinafter compound G].

1,2,3,9-tetrahydro-9-methyl-3-[(2-methyl-1H-imidazol-1-yl)methyl]-4H-carbazol-4-one (hereinafter compound H) in free base form or in acid addition patt form .[ER 38032F]

1-methyl-indazol-3-yl-carboxylic acid 9-methyl-9-aza-bicyclo[3.3.1]non-3α-yl-amide (hereinafter compound I), and especially compound E.

The compounds of the invention may be administered in free base form or, when they can be formed, in pharmaceutically acceptable acid addition salt form or in a quaternary ammonium salt form. Such salts may be prepared in conventional manner and are in general known. They exhibit the same order of activity as the free base form and pharmaceutical compositions comprise a compound of the invention in free base or pharmaceutically acceptable acid addition salt form or quaternary ammonium salt form in association with a pharmaceutical carrier or diluent. Such compositions may be manufactured in conventional manner.

The compounds may be administered by any conventional route, in particular enterally, preferably orally, e.g. in the form of tablets or capsules or parenterally, e.g. in the form of injectable solutions or suspensions.

Suitable pharmaceutical carriers and diluents for oral administration include polyethylene glycol, polyvinylpyrrolidone, mannitol, lactose etc. granulating agents, and disintegrating agents such as starch and algenic acid, binding agents such as stearic and gelatine, and lubricating agents such as magnesium stearate, stearic acid and talc. Suspensions may contain conserving agents like ethyl p-hydroxybenzoate, and suspending agents such as methyl-cellulose, tenside etc. For parenteral forms the compositions are preferably bufferred, aqueous solutions (pH between 4 and 5).

We have more over found that the compounds of the invention may be administered nasally and have an especially interesting resorption profile.

Furthermore the compounds of the invention increase the nasal resorption or bioavailability of other active agents such as peptides particularly when administered by the nasal route.

The compounds of the invention moreover are useful in the treatment of rhinitis and serotonin-induced nasal disorders as indicated by an inhibition of nasal secretions on administration of the compounds of the invention.

The testing may be effected as follows:

The bioavailability and pharmacokinetic profile of the compounds of the invention may be determined in conventional manner, e.g. in mammals including rhesus monkeys and humans. The concentrations of the compounds of the invention in the blood plasma after administration of from about 0.01 to about 10 mg/kg to each nostril, e.g. 7.5 mg in the case of compound E, locally to the nasal mucous membrane, e.g. as a spray, may be determined in conventional manner by e.g. radioimmunoassay or HPLC methods. The compounds of the invention are rapidly absorbed, e.g. over about 10 minutes.

Even after ca. 5 to 10 minutes following nasal administration, 200 ng of the compound indol-3-yl-carboxylic acid-endo- 8-methyl-8-aza-bicyclo[3,2,1]oct-3-yl ester may be detected in 1 ml of plasma. Upon oral administration, this concentration of active ingredient in the plasma is reached only after ca. 30 to 40 minutes. The general bioavailability of the compounds of the invention over a period of 6 hours is the same for nasal administration as for oral administration.

Nasal secretions are also inhibited. Additionally, the compounds of the invention when administered, e.g. at a dose of from 0.01 to 10 mg/kg with a therapeutically effective dosage of another compound, e.g. a peptide, such as salmon calcitonin increases the absorption thereof.

For example in the case of compound E (15 mg) and salmon calcitonin (100 IU) half of which is applied to each nostril, the bioavailability of salmon calcitonin (AUC up to 2 hours) is increased from 0.08 IV)/ml/hr plasma to 1.632 m IU/ml/hr/plasma in the rhesus monkey.

For the rhinitis and nasal serotonin-induced disorder indications, the appropriate dosage will, of course, vary depending upon, for example, the compound of invention employed, the host, the mode of administration and the nature and severity of the condition being treated. However, in general, satisfactory results are indicated to be obtained at daily dosages from about 0.01 mg/kg to about 10 mg/kg animal body weight. In humans, an indicated daily dosage for oral administration is in the range from about 5 mg to about 300 mg of a compound of formula I conveniently administered, for example, in divided doses up to four times a day, e.g. in the range of about 40 mg p.o. in the case of compound E.

When a compound of the invention is co-administered with another active agent, the appropriate dosage will, of course, vary depending upon, for example, the active agent of the compound of the invention and other active agent employed, the host, the mode of administration and the nature and severity of the condition being treated. However, in general, satisfactory results are indicated to be obtained at daily dosages from about one half to one tenth the usual dose of the other active agent. The compound of the invention is indicated to be administered at about one half to one tenth the usual dose.

The compounds of the invention may be administered for the rhinitis and nasal serotonin-induced disorders and for co-administration with another active agent, e.g. a peptide, by any conventional route, in particular enterally, preferably orally, e.g., in the form of tablets or capsules, or parenterally, e.g., in the form of injectable solutions or suspensions. The local application by the nasal route is preferred.

For the nasal administration route, the appropriate dosage will, of course, vary depending upon, for example, the compound of the invention employed, the host, and the nature and severity of the condition being treated. However, in general, satisfactory results in animals are indicated to be obtained at daily dosages from about 0.001 mg/kg to about 10 mg/kg animal body weight. In humans, an indicated dosage per actuation is in the range from about 0.01 mg to about 1 mg of a compound of the invention conveniently administered, for example, in doses up to four times a day.

Thus for gastrointestinal disorders or for migraine prophylaxis a compound according to the invention is indicated to be administered to the body nasally in a dosage of 0.13 to 0.4 mg kg body weight, i.e. ca. 10 to 30 mg or 1 to 3 pumps of the nasal spray per patient, and in order to control arrhythmia, it should be given in a dosage which is ca. 10 times higher, i.e. from 1.3 to 4 mg per kg body weight or 100 to 300 mg, or resp. 10 to 30 pumps of the nasal spray per patient.

The compound E is the preferred compound for the rhinitis and nasal route administration. It is indicated that compound E may be administered at daily dosages of about 0.1 mg nasally to humans.

The compounds of the invention may be administered nasally in any pharmacologically active form, e.g. in free base form, in acid addition salt form or in quaternary ammonium salt form.

The nasal mode of administration creates a simple method of administration which rapidly gives results and can be easily carried out by the patient himself, e.g. by administering a liquid form for nasal administration, for example a nasal spray or drop solution using a nasal applicator, or by inserting a gelatinous sponge or lyophilisate soaked in the active substance, or by blowing the galenic form in powder form into the nostrils.

The compounds of the invention may be present in the liquid form for nasal administration in a proportion of 1 to 30%, preferably 5 to 20%, especially 10 to 15% (weight/volume).

The present invention accordingly provides also a liquid form for nasal administration, containing 1) a compound of the invention 2) a preservative, especially benzalkonium chloride, and 3) a liquid diluent or a carrier, suitable for application to the nasal mucous membrane.

The proportion of benzalkonium chloride in the compositions according to the invention is preferably ca. 0.002 to ca. 0.02, especially ca. 0.01% (weight/volume) of the total composition.

In accordance with the invention, the above-mentioned forms of administration may be administered to the nasal mucous membrane, e.g. as drops or as a spray. As described hereinafter, however, they are preferably administered as a spray, i.e. as finely dispersed droplets. One further possible way of bringing the above-mentioned liquid form for nasal administration into contact with the nasal mucous membrane is to soak a gelatinous sponge (SPONGOSTAN) or lyophilisate with the substance and then to insert the sponge into the nostrils.

The liquid diluent or carrier employed is conveniently water (pharmaceutical grade). An aqueous salt solution is preferred in particular. The liquid forms for nasal administration according to the invention are formulated such that they allow administration to be effected nasally. With this in mind, they can e.g. also contain minimal amounts of further desired components or excipients, e.g. additional preservatives, or e.g. ciliary stimulants such as caffeine.

The liquid forms for nasal administration according to the invention preferably have a pH value of 5.5 to 6.

The liquid forms for nasal administration should also have an appropriate isotonicity and viscosity. They preferably have an osmotic pressure of ca. 260 to ca. 380 mOsm/liter. The desired viscosity of the compositions according to the invention depends on the relevant form of administration, e.g. whether nasal drops or a nasal spray are administered. For nasal drops, a viscosity of ca. 2 to ca. $40 \times 10^{-3}$ Pa.S is suitable. For nasal sprays, a viscosity of less than $2 \times 10^{-3}$ Pa.S is suitable.

If desired, the liquid forms for nasal administration may also contain further components, especially conventional pharmaceutically available surface-active agents. In this connection and as a further aspect of the present invention, it was found that the use of surface-active compounds in the nasal administration of the compounds of the invention increases their resorption through the nasal mucous membrane and improves the initial bio-availability. In this case, preference is given to non-ionic surface-active agents, for example polyoxyalkylene ethers of higher alcohols, e.g. of the general formula,

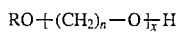

$$RO\text{+}(CH_2)_n\text{—}O\text{+}_xH$$

wherein RO signifies the radical of a higher alkanol, especially a higher alkanol such as lauryl or cetyl alcohol, or of an alkylphenol, or a sterol, especially lanosterol, dihydrocholesterol or cholesterol, as well as mixtures of two or several such ethers. Preferred polyoxyalkylene ethers which can be used for the present invention are polyoxyethylene- and polyoxypropylene-ethers (i.e. wherein n in the above-mentioned formula is 2 or 3), especially lauryl-, cetyl- and cholesterylpolyoxyethylene- and -polyoxypropylene-ethers, as well as mixtures of two or several such ethers.

Especially suitable polyethers for use according to the invention are those in which the average value of the recurring units in the polyoxyalkylene component (x in the above formula) lies between 4 and 75, especially between 8 and 30 and particularly between 16 and 26. The polyethers may be obtained in accordance with known methods. A large choice of such products is available commercially and is sold e.g. by Amerchol under the trade name Solulan (R), by KAO Soap, ICI and Atlas under the trade names Emalex (R), Brij (R) and Laureth (R), and by Croda under the trade name Cetomacrogol (R).

Examples of polyoxyalkylene ethers which are suitable for use according to the invention, e.g. (POE=polyoxyethylene ethers: POP=polyoxypropylene ether; x=average value of the recurring units in the POE/POP component) are listed in the following:

1. Cholesterylethers:
   1.1 Solulan(R) C-24—POE, x=24
2. Ethers of lanolin alcohols:
   2.1 Solulan(R) 16—POE, x=16
   2.2 Solulan(R) 26—POE, x=25
   2.3 Solulan(R) 75—POE, x=75
   2.4 Solulan(R) PB-10—PPE, x=10
   2.5 Solulan(R) 98—POE, x=10-partly acetylated
   2.6 Solulan(R) 97—POE, x=9-wholly acetylated
3. Laurylethers:
   3.1 Emalex(R) 709/Lauzeth (R) 9—POE, x=9
   3.2 Laureth(R) 4/Brij(R) 30—POE, x=4
   3.3 Laureth(R) 23/Brij(R) 35—POE, x=23
4. Cetylethers:
   4.1 Cetomacrogol (R)—POE, x=20 to 24

Lanolin alcohols are also known as wool fat alcohols and are a mixture of cholesterol, dihydrocholesterol and lanosterol.

Preferred polyethers for use according to the invention are cholesteryl polyoxyethylene ethers, e.g. polyethers of the above formula, wherein n=2 and RO is a cholesteryl radical, in particular polyethers wherein the number of recurring units in the polyoxyethylene component is 16 to 26, especially about 24.

These polyethers are, preferably free from impurities, and especially from other polyoxyalkylene ethers. They preferably contain at least 75%, most particularly at least 85% and especially at least 90% (weight) of the pure cholesteryl polyoxyethylene ether.

If a surface-active agent, e.g. a polyoxyalkylene ether, is used, the amount present in the compositions according to the invention will depend on the surface-active agent used in particular, the form of administration (e.g. drops or spray) and the desired effect.

In general, the amount of surface-active agent employed is between ca. 2.0 and ca. 200 (preferably up to ca. 100, especially up to ca. 20), especially between ca. 5 and ca. 30 (preferably up to ca. 15) and in particular ca. 10 mg/ml.

For nasal administration, the liquid forms for nasal administration are preferably placed in an applicator, which is equipped with a device that enables the composition to be applied to the nasal mucous membrane, e.g. a nasal spray applicator.

Such applicators are known per se and include those which are suitable for the administration of liquid preparations as drops or as a spray to the nasal mucous membrane. Since the dosing of the compounds of the invention should be as exact as possible, the use of spray applicators in which an exact control over the quantity administered is possible is generally preferred. Suitable appliance for administration are e.g. atomizers such as pump dispensers or aerosol cans. In the latter case, the applicator contains a composition according to the invention as well as a propellant which is suitable for use in a nasal spray applicator. The atomizer appliance is provided with an appropriate spray device which enables the composition to be applied to the nasal mucous membrane. Such devices are known in general.

The container, e.g. a nasal spray applicator, may contain a quantity of the composition which is sufficient for a single nasal dose or for administration of several doses, e.g. over a period of several days or weeks. The amounts of the individual doses will preferably correspond to the above-mentioned doses.

Applicators as defined above are preferably spray applicators for nasal usage. They preferably enable the composition contained there in to be administered in single doses of ca. 0.05 to ca. 0.15 ml, e.g. ca. 0.1 ml.

Suitable compositions, as well as the individual components 1,2 and 3 for use in an applicator, are those which have been previously described. The dosages which are suitable for use similarly correspond to the dosages given previously.

Furthermore, the invention relates to a process for the production of a liquid form for nasal administration, containing 1) compounds according to the invention
2) a preservative specially benzalkonium chloride, and
3) a liquid diluent or a carrier, which is suitable for administering to the nasal mucous membrane, as well as optionally a surface-active agent which is suitable for administering to the nasal mucous membrane characterised in that the components are intimately mixed together, and if desired, the composition obtained is placed in an applicator which is provided with a spray device which enables the composition thus obtained to be administered to the nasal mucous membrane. Furthermore, a sponge (SPONGO-STAN) may be soaked with the composition obtained and the soaked sponge can be inserted into the nostrils.

The stability of the composition according to the invention can be determined in the usual way.

The compositions according to the invention containing benzalkonium chloride are stable towards contamination by germs, e.g. as in standard tests such as those described by S. Urban et al. in Zbl. Bakt. Hyg. I Abt. Orig. B. 1972,478–484 (1981) and S. Urban, Acta Pharm. Technol.22,247–253 (1976). For example, the cell count of the standard bacteria, namely E. coli ATCC 8739, Pseud. aeruginosa ATCC 9027, Staph. aureus ATCC 6538, Strept. pyogenes ATCC 8668 and standard fungi Cand. albicans ATCC 10231, Sacch. cerevisae ATCC 9763, Aspergillus niger ATCC 16404 and Pen. steckil ATCC 10499, is reduced to 0.1% or less within 24 hours after injecting them with the composition, as can be shown in standard tests.

In a stability test, the nasal spray composition of the following example 1 was kept for 3 months at 30° C. under a nitrogen atmosphere in a glass container, Pseud. aeruginosa ATCC 9027, Staph. aureus ATCC 6538, Strept. pyogenes ATCC 8668 and the fungi and, albicans ATCC 10231, Sacch. cerevisae ATCC 9763, Aspergillus niger ATCC 16404 and Pen. stechii ATCC 10499 were added until a cell count of ca. $2\times10^5$ organisms was reached in the injected liquid. Within 2 hours, the germ count had reduced to less than 0.1%, Within 4 weeks, the germs could no longer be detected.

Equally favourable results are obtained if the compounds of the invention are administered in a galenic form, which is in the form of a powder and is introduced by blowing into the nostrils.

The compounds of the invention other than compounds of formula I wherein A is 3,5-dichlorophenyl, B is CO, C is O and D is tropanyl antagonise the pulmonary depressor reflex in animals.

The action of the compounds may be observed in spontaneously breathing rabbits which are anesthetized by a continuous infusion of sodium pentobarbital. Both vagi are intact and the systemie, arterial blood pressure, heart beat, breathing rate and platelet count are normal.

Pulmonary embolism is produced by injecting 1 mg Sephadex G-$^{25}$ beads suspended in 0.2 ml dextran (6%) in 1 minute intervals in 6 animals into the right atrium.

Pretreatment with the compounds of the invention i.v. at a dose of from 0.1 to 1 mg/kg produces a reduction in mortality and an improvement in the cardiovascular and breathing reflex parameters resulting during the developing lung embolism.

For this indication, the appropriate dosage will, of course, vary depending upon, for example, the compound of the invention employed, the host, the mode of administration and the nature and severity of the condition being treated. However, in general, satisfactory results in animals are indicated to be obtained at daily dosages from about 0.1 mg/kg to about 5 mg/kg animal body weight. In larger mammals, for example humans, an indicated daily dosage is in the range from about 5 mg to about 50 mg of a compound of the invention conveniently administered, for example, in divided doses up to four times a day, preferably parenterally.

The compounds are preferably administered in the form of a pharmaceutical composition e.g. as described above.

The compounds of the invention may be administered for the lung embolism, by any conventional route, in particular enterally (if appropriate), preferably orally, e.g., in the form of tablets or capsules, or parenterally (if appropriate), e.g., in the form of injectable solutions or suspensions, or by the nasal route.

The compounds of the invention also inhibit cancer therapy induced emesis in animals as indicated by standard tests, e.g. an inhibition of cis-platinin (10 mg/kg i.v.) induced emesis in ferrets at a dose of from about 0.005 to about 0.5 mg/kg i.v.

The compounds of the invention furthermore are useful in the treatment of other serotonin $HT_3$-induced gastro-intestinal disorders, e.g. as indicated in activity in tests indicated in EP 189002 at the same order of activity.

The compounds are useful in the treatment of disorders resulting from increased peristaltic movements in the intestines and intestinal disorders arising or from activation of 5-$HT_3$ receptors, including diarrhea, e.g. secretary diarrhea, bacterial induced diarrhea, choleic diarrhea, traveller's diarrhea and psychogenic diarrhea, Crohn's disease, spastic colon and irritable bowel syndrome. The compounds are also indicated to be useful in the treatment of disorders due to hypersecretion in the intestines, e.g. as a result of inflammation such as arising out of gastritis, peptic ulcer, biliary dyskinesia, appendicitis, ulcerative colitis and due to carcinoid syndrome leading to increased 5-HT secretion.

Furthermore, the compounds are useful in the treatment of disorders arising from decreased peristaltic movements in the stomach and/or stomach disorders arising from activation of 5-$HT_3$ receptors, including those arising from decreased gastric emptying, including treatment of oesophageal motility disturbances, achalasia, hiatus hernia, cardia insufficiency, gastrooesophageal and gastroduodeinal reflux, stomach hypotonia and pylorus hyperplasia.

The compounds are moreover useful in treatment of schizophrenia and mania and anxiety.

For all these indications, the compounds may be administered in the same manner as for the rhinitis indications and in the same manner as described in European Patent Publication No. 189002.

Toxicity and Tolerability:

Toxicity and Tolerability studies may be effected in conventional manner with the compounds of the invention to determine the upper dosage.

Toxicity studies may be effected for example in the rat and the dog over for example 26 weeks.

For compound E over 26 weeks the no toxic effect bowel in the dog was 5–20 mg/kg/daily p.o. For the rat it was 16 to 45 mg/kg per day p.o. Other compounds of the invention may have the same order of tolerability. In healthy human volunteers single doses up to 150 mg were well tolerated without relevant side effects.

The following examples illustrate the invention.

EXAMPLE 1

Tablets for oral administration

Tablets containing the constituents as specified below were produced in conventional manner and are used in the indications specified above.

| | |
|---|---|
| Compound E in form of hydrochloride (corresponding to 15 mg free base) | 16.9 mg |

-continued

| | |
|---|---|
| Hydroxypropylcellulose | 1.2 mg |
| Corn Starch | 12.0 mg |
| Lactose | 92.8 mg |
| Silica | 0.6 mg |
| Magnesium stearate | 1.5. mg |
| Tablet weight | 125.0 mg |

EXAMPLE 2

Capsules for oral administration

Capsules containing the constituents as specified below are produced in conventional manner and are used in the indications specified above.

| | |
|---|---|
| 1-methyl-N (-endo-9-methyl-9-aza-bicyclo-[3.3.1] indol-3-yl) carboxylic acid amide in form of the hydrochloride corresponding to 15 mg base) | 16.9 mg |
| Lactose | 28.7 mg |
| Silica | 1.5 mg |
| Magnesium stearate | 3 mg |
| Capsule content weight of | 50.1 mg |

EXAMPLE 3

Injection solution for i.v. administration

A composition for injection is made up in conventional manner and is used at a dose of 10 mg a day.

| | A | B | C |
|---|---|---|---|
| Compound E in form of hydrochloride | 1.13[1] | 2.256[2] | 11.282[3] |
| Acetic acid (99 to 100%)* | 1.2 | 0.6 | 0.6 |
| Sodium acetate 3. H$_2$O* | 1.8 | 3.18 | 3.18 |
| Sodium chloride | 8 | 7.5 | 6.5 |
| Water for injection to | 1.0 ml | | |

[1] = 1 mg free base,
[2] = 2 mg free base,
[3] = 10 mg free base
pH value 4.3;
*Buffer used 1/30 molar

EXAMPLE 4

Capsules for oral administration 5 mg and 15 mg capsules (A and B respectively) containing the constituents as specified below were produced in conventional manner and are used in the indications specified above 2–4 times a day in the case of A and once a day in the case of B.

| | A mg | B mg |
|---|---|---|
| Compound E in form of hydrochloride | 5.641 | 16.92 |
| Lactose 200 mesh | 84.929 | 79.29 |
| Lactose 100 mesh | 84.43 | 79.29 |
| Corn starch | 120.00 | 120.00 |
| Silica | 1.5 | 1.5 |
| Magnesium stearate | 3.0 | 3.0 |
| | 300 mg | 300 mg |

Capsules containing other weights can be formulated in conventional manner.

EXAMPLE 5

Nasal liquid Composition

| Components | Quantity of components |
|---|---|
| indol-3-yl-carboxylic acid-endo-8-methyl-8-aza-bicyclo[3.2.1]oct-3-yl-ester. HCl | 100 mg |
| benzalkonium chloride | 0.1 mg |
| NaCl (0.9% aqueous solution) | 0.6 ml |
| distilled water | 0.4 ml |

The solution obtained is filtered (e.g. through a 0.2 μm filter) and filled into a nasal canister, or a gelatinous foam (SPONGOSTAN) is soaked with the solution. It is administered e.g. for the treatment of rhinitis, lung embolism or to improve the absorption of other active agents.

EXAMPLE 6

Nasal liquid Composition

| Components | Quantity of components |
|---|---|
| 1-methyl-N-endo-9-methyl-9-azabicyclo-[3.3.1]indol-3-yl-carboxylic acid amide | 50 mg |
| benzalkonium chloride | 0.1 mg |
| NaCl (0.9% aqueous solution) | 0.83 ml |
| distilled water | 0.17 ml |

The solution obtained is filtered (e.g. through a 0.2 μm filter) and filled into a nasal spray canister, or a gelatinous foam (SPONGOSTAN) is soaked with the solution. It is administered in analogous manner to that disclosed, in example 5.

The active agents in Examples 1 to 6 may be replaced by the following compounds of formula I wherein:

| | A = II | B = —CO— | | | | | n (VI) D = | |
|---|---|---|---|---|---|---|---|---|
| No. | $R_1$ | $R_2$ | Z | CO-Position | C | Conf. | VIII (pos.) | $R_8$ |
| 1 | H | H | NH | 3 | NH | endo | 3 (VI) | $CH_3$ |
| 2 | 5-F | H | $NCH_3$ | 3 | O | endo | 3 (VI) | H |
| 3 | H | 2-Cl | NH | 3 | O | endo | 2 (VI) | $CH_3$ |
| 4 | H | 2-$OCH_3$ | NH | 3 | O | endo | 2 (VI) | $CH_3$ |
| 5 | H | 3-I | NH | 4 | O | endo | 2 (VI) | $CH_3$ |
| 6 | H | H | NH | 4 | O | endo | 2 (VI) | $CH_3$ |
| 7 | H | H | NH | 4 | O | endo | 3 (VI) | $CH_3$ |
| 8 | 5-Cl | H | NH | 3 | O | endo | 2 (VI) | $CH_3$ |
| 9 | 4-$OCH_3$ | H | NH | 3 | O | endo | 2 (VI) | $CH_3$ |
| 10 | 5-$OCH_3$ | H | NH | 3 | O | endo | 2 (VI) | $CH_3$ |
| 11 | H | H | $NCH_3$ | 3 | O | endo | 2 (VI) | $CH_3$ |

-continued

| No. | $R_1$ | $R_2$ | Z | Carbonyl Position | C | Conf. | n (VI) D = VIII (pos.) | $R_8$ |
|---|---|---|---|---|---|---|---|---|
| 12 | H | H | NH | 3 | O | exo | 2 (VI) | $CH_3$ |
| 13 | 5-F | H | NH | 3 | NH | endo | 2 (VI) | $CH_3$ |
| 14 | H | H | $NCH_3$ | 3 | NH | endo | 2 (VI) | $CH_3$ |
| 15 | H | 2-$CH_3$ | NH | 3 | NH | endo | 2 (VI) | $CH_3$ |
| 16 | H | H | NH | 3 | NH | exo | 2 (VI) | $CH_3$ |
| 17 | H | H | NH | 3 | NH | endo | 2 (VI) | $CH_3$ |
| 18 | 5-Cl | H | NH | 3 | H | endo | 2 (VI) | $CH_3$ |
| 19 | H | H | NH | 3 | O | endo | 3 (VI) | Bz |
| 20 | H | H | $NCH_3$ | 3 | O | endo | 3 (VI) | Bz |
| 21 | 5-F | H | NH | 3 | O | endo | 3 (VI) | Bz |
| 22 | H | H | S | 3 | O | endo | 3 (VI) | $CH_3$ |
| 23 | H | H | S | 3 | NH | endo | 3 (VI) | $CH_3$ |
| 24 | H | H | O | 3 | NH | endo | 3 (VI) | $CH_3$ |
| 25 | H | H | O | 3 | O | endo | 3 (VI) | $CH_3$ |
| 26 | H | H | $CH_2$ | 3 | NH | endo | 3 (VI) | $CH_3$ |

| No. | A = II, $R_1$ | B = —CO— $R_2$ | Z | Carbonyl Position | C | Conf. | n (VI) D = VIII (pos.) | $R_8$ |
|---|---|---|---|---|---|---|---|---|
| 27 | H | H | NH | 3 | NH | exo | 4 (VI) | $CH_3$ |
| 28 | H | H | NH | 3 | O | exo | 4 (VI) | $CH_3$ |
| 29 | H | H | NH | 3 | O | endo | 3 (VI) | $CH_3$ |
| 30 | H | H | NH | 3 | O | endo | 2 (VI) | n-$C_3H_7$ |
| 31 | H | H | NH | 3 | O | exo | 2 (VI) | Bz |
| 32 | H | H | NH | 3 | O | endo | 2 (VI) | Bz |
| 33 | H | H | NH | 3 | O | endo | 2 (VI) | H |
| 34 | 5-F | H | NH | 3 | O | endo | 3 (VI) | H |
| 35 | H | H | $NCH_3$ | 3 | O | endo | 3 (VI) | H |
| 36 | H | H | NH | 3 | O | endo | 3 (VI) | H |
| 37 | 5-$CH_3$ | H | NH | 3 | O | endo | 3 (VI) | $CH_3$ |
| 38 | H | 2-$CH_3$ | NH | 3 | O | endo | 3 (VI) | $CH_3$ |
| 39 | 5-F | H | $NCH_3$ | 3 | O | endo | 3 (VI) | $CH_3$ |
| 40 | 5-F | H | NH | 3 | O | endo | 3 (VI) | $CH_3$ |
| 41 | 5-F | H | $NCH_3$ | 3 | O | endo | 3 (VI) | Bz |
| 42 | H | H | $NCH_3$ | 3 | O | endo | 3 (VI) | $CH_3$ |
| 43 | 5-$CH_3$ | H | NH | 3 | NH | endo | 3 (VI) | $CH_3$ |
| 44 | H | H | NH | 5 | O | endo | 2 (VI) | $CH_3$ |
| 45 | H | H | NH | 5 | O | endo | 3 (VI) | $CH_3$ |
| 46 | H | 3-I | NH | 5 | O | endo | 3 (VI) | $CH_3$ |
| 47 | H | H | NH | 4 | NH | exo | 2 (VI) | $CH_3$ |
| 48 | H | H | NH | 4 | NH | endo | 2 (VI) | $CH_3$ |
| 49 | H | H | NH | 5 | H | endo | 2 (VI) | $CH_3$ |
| 50 | H | H | NH | 3 | O | — | VIII (3) | — |

| No. | A = III, $R_4$ | B = —CO— $R_5$ | $R_6$ | $R_7$ | C | Conf. | n (VI) D = VIII (pos.) | $R_8$ |
|---|---|---|---|---|---|---|---|---|
| 51 | $OCH_3$ | H | $NHCH_3$ | Cl | O | — | VIII (3) | — |
| 52 | $OCH_3$ | H | $NH_2$ | Cl | O | — | 2 (VI) | Bz |
| 53 | $OCH_3$ | H | $NH_2$ | Cl | O | exo | 2 (VI) | H |
| 54 | $OCH_3$ | H | $NHCH_3$ | Cl | O | endo | 2 (VI) | $CH_3$ |
| 55 | $OCH_3$ | H | $N(CH_3)_2$ | H | O | exo | 2 (VI) | Bz |
| 56 | $OCH_3$ | H | $NH_2$ | Cl | O | endo | 2 (VI) | $CH_3$ |
| 57 | $OCH_3$ | H | $NH_2$ | Cl | O | endo | 2 (VI) | H |
| 58 | $OCH_3$ | H | $NH_2$ | H | O | endo | 2 (VI) | H |
| 59 | $OCH_3$ | H | $NH_2$ | H | O | exo | 2 (VI) | H |
| 60 | $OCH_3$ | H | $NH_2$ | H | O | endo | 2 (VI) | $CH_3$ |
| 61 | $OCH_3$ | H | $N(CH_3)_2$ | H | O | endo | 2 (VI) | $CH_3$ |
| 62 | Cl | H | $NH_2$ | H | O | endo | 2 (VI) | $CH_3$ |
| 63 | $OCH_3$ | I | $NH_2$ | H | O | endo | 2 (VI) | $CH_3$ |
| 64 | $OCH_3$ | I | $NHCH_3$ | H | O | endo | 3 (VI) | $CH_3$ |
| 65 | $OCH_3$ | H | $NHCH_3$ | H | O | endo | 3 (VI) | $CH_3$ |
| 66 | Cl | H | $NO_2$ | H | O | endo | 2 (VI) | $CH_3$ |
| 67 | $OCH_3$ | H | Br | H | O | endo | 2 (VI) | $CH_3$ |
| 68 | H | Cl | H | Cl | O | endo | 3 (VI) | $CH_3$ |
| 69 | $OCH_3$ | H | 1-Pyrrolyl | Cl | O | endo | 2 (VI) | $CH_3$ |
| 70 | $OCH_3$ | H | 1-Pyrrolyl | H | O | endo | 2 (VI) | $CH_3$ |
| 71 | $OCH_3$ | H | $NHCH_3$ | Cl | NH | — | VIII (3) | — |
| 72 | H | Cl | H | Cl | Cl | — | VIII (3) | — |
| 73 | $OCH_3$ | H | $NH_2$ | Cl | NH | — | VIII (3) | — |

| No. | Formula II, $R_1$ | B = —CO— $R_2$ | Z | Carbonyl Position | C | Conf. | D = Group | $R_8$ |
|---|---|---|---|---|---|---|---|---|
| 74 | H | H | NH | 3 | O | exo | (X) | — |
| 75 | H | H | NH | 3 | O | endo | (XVII) (Z = $OCH_3$)* | $CH_3$ |
| 76 | H | H | NH | 3 | O | (endo) | (XVI) (l = 3) | $CH_3$ |

-continued

| No. | | | | | | | | | | |
|---|---|---|---|---|---|---|---|---|---|---|
| 77 | H | H | NH | 3 | | O | endo | (XI) | | CH$_3$ |
| 78 | H | H | NH | 3 | | O | (endo) | (XVI) (l = 3) | | CH$_3$ |
| 79 | H | H | NH | 3 | | O | (exo) | (XVI) (l = 3) | | CH$_3$ |
| 80 | H | H | NH | 3 | | O | endo | (X) | | — |
| 81 | H | H | NH | 3 | | O | exo | (XIII) (t = 1) | | CH$_3$ |
| 82 (−) | H | H | NH | 3 | | O | endo | (XI) | | CH$_3$ |
| 83 (+) | H | H | NH | 3 | | O | endo | (XI) | | CH$_3$ |
| 84 | H | H | NH | 3 | | O | endo | (XII) | | CH$_3$ |
| 85 | H | H | NH | 5 | | O | endo | (XVII) (Z = OCH$_3$)* | | CH$_3$ |

( ) = Ring is in Chairform
* = (1s*, 3r*, 5R*, 6R*)
Bz in R$_8$ = Benzyl

| No. | A = III, B = −CO− R$_4$ | R$_5$ | R$_6$ | R$_7$ | C | Conf. | n (VI) D = VIII (pos.) | R$_8$ |
|---|---|---|---|---|---|---|---|---|
| 86 | OCH$_3$ | H | NHCH$_3$ | Cl | NH | exo | D = Group | — |
| 87 | OCH$_3$ | H | NHCH$_3$ | Cl | NH | endo | D = Group | — |

| No. | Formula II, B = −CO− R$_1$ | R$_2$ | Z | Carbonyl Position | C | Conf. | Formula XVIII R$_8$ | R$_9$ | R$_{10}$ | R$_{11}$ | R$_{12}$ | m | n | o | p |
|---|---|---|---|---|---|---|---|---|---|---|---|---|---|---|---|
| 88 (−) | H | H | −NH− | 3 | −O− | S | CH$_3$ | H | H | — | — | 2 | 0 | 0 | 1 |
| 89 | H | H | −NH− | 3 | −O− | R | CH$_3$ | H | H | — | — | 2 | 0 | 0 | 1 |
| 90 | H | H | −NH− | 3 | −O− | RS | CH$_3$ | H | H | H | H | 1 | 0 | 1 | 0 |
| 91 | H | H | −NH− | 3 | −O− | RS | CH$_3$ | H | H | H | H | 0 | 1 | 1 | 1 |
| 92 | H | H | −NH− | 3 | −O− | RS | CH$_3$ | H | H | H | H | 2 | 0 | 1 | 0 |
| 93 | H | H | −NH− | 3 | −O− | RS | CH$_3$ | H | H | H | H | 1 | 1 | 1 | 0 |
| 94 | H | H | −NH− | 3 | −O− | RS | H | CH$_3$ | CH$_3$ | CH$_3$ | CH$_3$ | 1 | 1 | 1 | 0 |
| 95 | H | H | −NH− | 3 | −O− | RS | CH$_3$ | H | H | H | H | 2 | 1 | 1 | 0 |
| 96 | H | H | −NH− | 3 | −NH− | RS | H | H | H | H | H | 1 | 0 | 1 | 0 |
| 97 | H | H | −NH− | 3 | −NH− | RS | CH$_3$ | H | H | H | H | 1 | 0 | 1 | 0 |

| No. | Formula III, B = −CO− R$_4$ | R$_5$ | R$_6$ | R$_7$ | C | Conf. | Formula XVIII R$_8$ | R$_9$ | R$_{10}$ | R$_{11}$ | R$_{12}$ | m | n | o | p |
|---|---|---|---|---|---|---|---|---|---|---|---|---|---|---|---|
| 98 | OCH$_3$ | H | NH$_2$ | Cl | NH | RS | H | H | H | H | H | 1 | 0 | 1 | 0 |
| 99 | OCH$_3$ | H | NHCH$_3$ | Cl | NH | RS | CH$_3$ | H | H | H | H | 0 | 1 | 1 | 1 |

| No. | A = Group of Formula | R$_1$ | R$_2$ | X−Y | Z | B | Position of B | C | D = Group of Formula | Position of g | Conf. | n | R$_8$ |
|---|---|---|---|---|---|---|---|---|---|---|---|---|---|
| 100 | (II) | H | H | — | NH | CO | (3) | O | (VII) | | anti | 3 | CH$_3$ |
| 101 | (II) | H | H | — | NH | CO | (3) | O | (VII) | | syn | 3 | CH$_3$ |
| 102 | (IV) | H | H | N=CH | — | CO | (3) | O | (VI) | | α | 3 | CH$_3$ |
| 103 | (V) | H | — | — | — | CO | (3) | O | (VI) | | α | 3 | CH$_3$ |
| 104 | (IV) | H | H | CH=CH | — | CO | (2) | O | (VI) | | α | 3 | CH$_3$ |
| 105 | (IV) | H | H | O−CH$_2$ | — | CO | (3) | O | (VI) | | α | 3 | CH$_3$ |
| 106 | (II) | H | H | — | NH | CO | (3) | O | (IX) | | (1S*, 5R*, 6R*) | — | CH$_3$ |
| 107 | (II) | H | H | — | NH | CO | (3) | NH | (VI) | | anti | 3 | CH$_3$ |

| No. | | R$_4$ | R$_5$ | R$_6$ | R$_7$ | | | | | | | | |
|---|---|---|---|---|---|---|---|---|---|---|---|---|---|
| 108 | (III) | H | H | CH$_3$ | H | SO$_2$ | — | O | (VIII) | 3 | RS | — | — |
| 109 | (III) | H | H | CH$_3$ | H | SO$_2$ | — | NH | (VIII) | 3 | RS | — | — |
| 110 | (III) | H | O‖ −C−NH$_2$ | H | H | CO | — | NH | (VIII) | 3 | RS | — | — |
| 111 | (III) | OCH$_3$ | H | H | SO$_2$NH$_2$ | CO | — | NH | (VIII) | 3 | RS | — | — |
| 112 | (III) | H | H | H | SO$_2$NH$_2$ | CO | — | NH | (VIII) | 3 | RS | — | — |

| No. | A = II R$_1$ | R$_2$ | B = CO Z | Carbonyl Position | C | Conf. | D Group of Formula | q | R$_{13}$ | R$_{14}$ | mp. (°C) |
|---|---|---|---|---|---|---|---|---|---|---|---|
| 113 | H | H | NH | 2 | NH | — | XIX | 2 | C$_2$H$_5$ | C$_2$H$_5$ | 133–134 |
| 114 | H | H | NH | 3 | NH | — | XIX | 2 | C$_2$H$_5$ | C$_2$H$_5$ | 109–110 |
| 115 | H | H | NH | 4 | NH | — | XIX | 2 | C$_2$H$_5$ | C$_2$H$_5$ | 143–144 |
| 116 | H | H | NH | 6 | NH | — | XIX | 2 | C$_2$H$_5$ | C$_2$H$_5$ | 104–105 |
| 117 | H | H | NH | 7 | NH | — | XIX | 2 | C$_2$H$_5$ | C$_2$H$_5$ | 78,5–79,5 |
| 118 | H | H | NH | 5 | O | — | XIX | 2 | C$_2$H$_5$ | C$_2$H$_5$ | 178–179 (Dec.) (Oxalate) |
| 119 | H | 3-Br | NH | 5 | NH | — | XIX | 2 | C$_2$H$_5$ | C$_2$H$_5$ | 131–132 |
| 120 | H | 3-I | NH | 5 | NH | — | XIX | 2 | C$_2$H$_5$ | C$_2$H$_5$ | 126–127 |

-continued

| | | | | | | | | | | | | |
|---|---|---|---|---|---|---|---|---|---|---|---|---|
| 121 | H | 3-CH₃ | NH | 5 | | NH | — | XIX | | 2 | C₂H₅ | C₂H₅ | 106–107 |
| 122 | H | H | NCH₃ | 5 | | NH | — | XIX | | 2 | C₂H₅ | C₂H₅ | 139–140 |

| | A = III, B = CO | | | | | | n (VI) | | |
|---|---|---|---|---|---|---|---|---|---|
| No. | $R_4$ | $R_5$ | $R_6$ | $R_7$ | C | Conf. | D = (VIII) (pos.) | $R_8$ | mp. (°C.) |
| 123 | H | Cl | H | Cl | O | — | 3 (VI) | CH₃ | 170–171 (Malonate) |
| 124 | H | Cl | H | Cl | O | — | (VIII) 3 | — | 159–160 (Malonate) |

| | A = II, B = CO | | | Carbonyl | | | | |
|---|---|---|---|---|---|---|---|---|
| No. | $R_1$ | $R_2$ | Z | Position | C | Conf. | D = (XX) (pos.) | mp. (°C.) |
| 124 | H | H | NH | 3 | O | 2R*,3S* | (XX) 3 | 230–232 (Dec.) |
| 125 | H | H | NH | 3 | O | 2S*,3S* | (XX) 3 | 270–272 (Dec.) (Hydrochloride) |

| | A = IIa, B = CO | | | Carbonyl | | D = (VIII) (pos.) | | |
|---|---|---|---|---|---|---|---|---|
| No. | $R_1$ | $R_2$ | Z | Position | C | n (VI) | $R_8$ | mp. (°C.) |
| 127 | H | H | NH | 5 | NH | (VIII) 3 | — | 271–272 |
| 128 | 6-OCH₃ | H | NH | 3 | CH₂ | 2 (VI) | H | 279–281 |
| | A = IIb, B = CO | | | | | D = n (VI) | | |
| 129 | H | H | — | 3 | O | 2 (VI) | CH₃ | 248–250 (Dec.) (Hydrochloride) |
| | A = IIc, B = CO | | | | | D = n (VI) | | |
| 130 | H | H | — | 3 | O | 2 (VI) | CH₃ | 112–113 |
| 131 | H | H | — | 3 | NH | 3 (VI) | CH₃ | Described Europ. Pat. App. No. 200 444 |

| | A = IId, B = CO | | | Carbonyl | | D = (VIII) (pos.) | | |
|---|---|---|---|---|---|---|---|---|
| No. | $R_1$ | $R_2$ | Z | Position | C | n (VI) | $R_8$ | mp. (°C.) |
| 132 | — | — | — | 2 | O | 3 (VI) | CH₃ | 242–243 (Hydrochloride) |
| 133 | | | | 3 | O | 3 (VI) | CH₃ | 233–234 (Hydrochloride) |
| | A = II, B = CO | | | | | | | |
| 134 | H | H | NH | 3 | NCH₃ | 3 (VI) | CH₃ | 247–248 (Hydrogenoxalate) |

| | A = II, B = CO | | | Carbonyl | | | | |
|---|---|---|---|---|---|---|---|---|
| No. | $R_1$ | $R_2$ | Z | Position | C | Conf. | D | mp. (°C.) |
| 135 | H | H | S | 3 | O | 9s | (XXI) | 176 |
| 136 | H | H | S | 3 | O | 9r | (XXI) | 125 |

| | A = III, B = CO | | | | | | | | |
|---|---|---|---|---|---|---|---|---|---|
| No. | $R_4$ | $R_5$ | $R_6$ | $R_7$ | C | Conf. | D | $R_8$ | mp. (°C.) |
| 137 | OCH₃ | H | NH₂ | Cl | NH | MESO | (XXII) | CH₃ | 232–234 (Dec.) (Hydrochloride) |

| | A = II, B = CO | | | Carbonyl | | | | | |
|---|---|---|---|---|---|---|---|---|---|
| No. | $R_1$ | $R_2$ | Z | Position | C | Conf. | D = n (VI) | $R_8$ | mp. (°C.) |
| 138 | 6-OCH₃ | H | NH | 3 | O | MESO | 2 (VI) | CH₃ | 243–244 (Hydrochloride) |
| 139 | 6-OH | H | NH | 3 | O | MESO | 2 (VI) | CH₃ | 290 (Dec.) (Hydrochloride) |
| 140 | 5-CH₃ | H | NH | 3 | O | MESO | 2 (VI) | CH₃ | 284–286 (Dec.) (Hydrochloride) |
| 141 | H | H | NH | 3 | — | MESO | 2 (VI) | CH₃ | 278–280 (Dec.) (Hydrochloride) |
| | A = II, B = CO | | | | | | D = | | |
| 142 | H | H | NH | 3 | O | ENDO | (XXIII) | CH₃ | 274–276 (Dec.) (Hydrochloride) |
| | A = II, B = CO | | | | | | D = | | |
| 143 | H | H | NH | 3 | O | MESO | (XXII) | CH₃ | 262–263 (Dec.) (Hydrochloride) |

-continued

| No. | A = IIe, B = CO R₁ | R₂ | Z | Carbonyl Position | C | Conf. | D = n (VI) | R₈ | mp. (°C.) |
|---|---|---|---|---|---|---|---|---|---|
| 144 | — | — | NH | 3 | O | — | 2 (VI) | CH₃ | 181–184 (Malonate) |
| 145 | A = II, B = CO H | H | NH | 3 | — | — | D = (XXIVa) | CH₃ | 221–223 |
| 146 | H | H | NH | 3 | — | — | D = (XXIVb) | CH₃ | 230 |
| 147 | H | H | 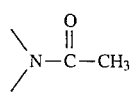 | 3 | O | ENDO | D = n (VI) 2 (VI) | CH₃ | 170–171 |
| 148 | 6-OH | H | NH | 3 | CH₂ | MESO | 2 (VI) | H | >280 |

| No. | A = III, B = CO R₄ | R₅ | R₆ | R₇ | Carbonyl Position | C | Conf. | D = XXI | | |
|---|---|---|---|---|---|---|---|---|---|---|
| 149 | OCH₃ | H | NH₂ | Cl | — | NH | — | XXV | | known from Europ. Patent appl. 94 742 |

Compound of formula Ia wherein
150    $R_{15} = CH_3$, $R_{16} = CH_3$ and $R_{17}$ and $R_{18} = H$    described in Brit. Patent appl. 2153821A    mp. 229–230° C.

The above compounds charaterised by the melting point are new (except where otherwise stated). They can be produced according to the processes described in Belgian Patents 897 117 and 903 984 as well as the following reference examples:

Reference example for the preparation of the compound No. 147

1-Acetyl-1H-indol-3-carboxylic acid 8-methyl-8-azabicyclo[3.2.1]oct-3α-yl-ester 2.84 g 1H-indol-3-carboxylic acid 8-methyl-8-azabicyclo [3.2.1]oct-3α-yl-ester are dissolved at 30° in 30 ml tetrahydrofuran. The solution is cooled to 0° and treated at this temperature dropwise with 5.9 ml butyl-lithium within 15 minutes. A slightly exothermic reaction takes place. The mixture is stirred at 0° for 1 hour, then cooled to −10° and treated dropwise with a solution of 0.75 ml acetyl chloride in 4 ml tetrahydrofuran. The mixture is stirred overnight at room temperature and then partitioned between 2N aqueous sodium carbonate solution and $CH_2Cl_2$. The organic phase is evaporated to give the title compound, which crystallizes from $CH_2Cl_2/C_2H_5OH$, m.p. 170°–171°.

Reference example for the preparation of the compound No. 113

N-[2-(N,N-Diethylamino)ethyl]indol-2-carboxamide

To a suspension of 4.83 g indol-2-carboxylic acid and 3.8 g N-hydroxy-succinimide in 60 ml abs. acetonitrile is added at room temperature a solution of 6.8 g dicyclohexyl-carbodiimide in 30 ml abs. diethyl ether, whereby the temperature rises rapidly to 33°. The suspension goes into solution and urea precipitates. The mixture is stirred at room temperature for 3 hours, filtered and the filtrate washed with acetonitrile. The filtrate is treated dropwise with 8.5 ml (60 mM) diethyl-aminoethyl amine, whereby the temperature rises from 20° to 28°. The mixture is left overnight and then is partitioned between 1N aqueous sodium carbonate solution and $CH_2Cl_2$. The organic phase is evaporated to give the title compound, recrystallised from $CH_2Cl_2$/hexane m.p. 133°–134°.

Reference example for the preparation of the compound No. 141

Indol-3-carbonyl-8-methyl-8-azabicyclo[3.2.1] oct-3β-yl-ane a) 3-Chloro-8-methyl-8-azabicyclo[3.2.1]octane To a solution of 95 g pseudotropine in 420 ml abs. $CHCl_3$ are added dropwise at 0° 195 ml thionyl chloride within 20 minutes. The reaction mixture is refluxed for 4 hours, then left overnight at room temperature and then heated to 60°–65° for 3 hours. The mixture is then diluted with $CH_2Cl_2$ to a volume of ca. 100 to 150 ml and poured on ice-water. A 35% aqueous NaOH solution is added to a pH 11 and then dry ice to a pH 10. After extraction with $CH_2Cl_2$ and distillation of the extracts (second fraction~97°–98°) the title compound is obtained.

b) 3-Cyano-8-methyl-8-azabicyclo[3.2.1]octane

To a solution of 18.16 g KCN in 28 ml $H_2O$ is added a solution of 42 g of the step a) compound in 90 ml ethanol and the mixture heated to 80°. Thereafter the mixture is refluxed for 22 hours. The mixture is evaporated to about ¼ of its volume in a rotatory evaporator, then rendered alkaline with potassium carbonate and extracted with ether. Distillation of the residue yields at about 0.4 mm Hg and 85° the title compound.

c) 3-Methoxycarbonyl-8-methyl-8-azabicyclo[3.2.1]octane

To 30 g of the step b) compound in 300 ml methanol and 3.7 ml water is introduced within 1 hour gaseous HCl, whereby the temperature rises to 60° (cooling). The mixture is left at room temperature for 18 hours. The resulting white suspension is filtered, the filtrate is concentrated, rendered alkaline with potassium carbonate to a pH 10 and extracted with ether (3 times). The ether phase is washed with water and evaporated to give the title compound, as an oil, b.p. 72°–74°/0.13–0.15 mm Hg.

d) 3-Carboxy-8-methyl-8-azabicyclo[3.2.1]octane

A solution of 25.2 g of the step c) compound in 20 ml methanol is treated portionwise with 70 ml 2N aqueous NaOH solution within 30 minutes (pH at the end 13.2). The mixture is left at room temperature for 3 hours and then treated with the same amount of 2N HCl to a pH 5.8. The reaction mixture is chromatographed on about 300 ml amberlite TR 120 (H+form) using 10% $NH_3$ as eluant to give the title compound (recrystallised from ethanol/hexane), m.p. 222°–224° (decomp.).

e) 3-Chloro-carbonyl-8-methyl-8-azabicyclo[3.2.1]octane

To a solution of 4.22 g. of the step d) compound in 50 ml $CH_2Cl_2$ are added dropwise at about 15° 2.8 ml oxalyl chloride diluted with 5 ml $CH_2Cl_2$. The resulting white suspension is stirred 30 minutes at room temperature, diluted with 50 ml hexane, filtered and washed with $CH_2Cl_2$/hexane (1:2), to yield the hydrochloride of the title compound, decomp. from 205°.

f) Indol-3-carbonyl-8-methyl- 8-azabicyclo[3.2.1]oct-3β-yl-ane

To a Grignard reagent prepared from 1.44 g magnesium, 3.75ml methyl iodide and 55 ml abs. ether is added dropwise at boiling temperature a solution of 3.51 g indole in 20 ml abs. ether. The resulting silver grey mixture is refluxed for 1 hour, then cooled to 0° and treated portionwise with 6.72 g of the hydrochloride of the step e) compound, under slight exothermic reaction. A resin precipitates. The mixture is allowed to come to room temperature, whereby the resin solidifies. After leaving overnight water and $CH_2Cl_2$ are added. Stirring is effected until a white suspension results, which is extracted with $CH_2Cl_2$ (3 times). The aqueous phase is extracted with $CH_2Cl_2$ and 10 to 15% $C_2H_5OH$ (5 times). The evaporated exotracts (about 5 g) are dissolved in $CH_2Cl_2+10\%$ $CH_3OH$ and filtered (residue about 2 g). The solution is chromatographed on 250 g silica gel KG 004 using $CH_2Cl_2+10\%$ $C_2H_5OH$ as an eluant whereby the title compound is obtained (800 g). The residue and 800 mg of the compound obtained by chromatography are together recrystalized from $H_2O/C_2H_5OH$ to give the hydrochloride of the title compound, m.p. 278°–280° (decomp.).

Reference example for the preparation of the compound No. 148

3-(6-Hydroxyindolyl)-8-azabicyclo[3.2.1]-3β-methyl-ketone a) 8-Benzyl-8-azabicyclo[3.2.1]octane-3β-acetic acid ethyl ester

To 14 g 3-carbethoxy-methylen-8-benzyl-8-azabicyclo [3.2.1]octane in 300 ml aqueous $NH_3$ and 100 ml toluene at −40° are added 2.5 g sodium. The resulting blue mixture is decomposed after 5 minutes with solid $NH_4Cl$ and the $NH_3$ is distilled off. After addition of water the mixture is extracted with $CH_2Cl_2$ and chromatographed on silicium dioxide with ethyl acetate/hexane (1:8) to yield the title compound as a colourless oil.

b) 8-Azabicyclo[3.2.1]octane-3β-acetic acid ethyl ester

To a solution of 8.4 g of the step a) compound in 350 ml $C_2H_5OH$ are added 1 g Pd/C and the mixture is hydrogenated 4 hours. The mixture is filtered and evaporated to give the title compound as a colourless oil.

c) 8-Benzyloxycarbonyl-8-azabicyclo[3.2.1]-3β-acetic acid ethyl ester 5.7 g of the step b) compound, 100 ml toluene and 7.5 ml triethylamine are treated with 12.3 ml chloroformic acid benzyl ester. The mixture is heated 3 hours to 50°, then poured into 200 ml 0.1N HCl and extracted 3 times with $CH_2Cl_2$. The organic phase is dried ($Na_2SO_4$) and evaporated to give the title compound as a colourless oil.

d) 8-Benzyloxycarbonyl-8-azabicyclo[3.2.1]-3β-acetic acid 9.1 g of the step c) compound are dissolved in 60 ml ethanol, treated with 60 ml 2N aqueous NaOH solution and refluxed 1 hour. After removal of ethanol by distillation, the remaining aqueous phase is acidified by addition of 10% tartaric acid and extracted with $CH_2Cl_2$. The combined organic phases are dried and evaporated to give the title compound as a yellowish foam.

e) 8-Benzyloxycarbonyl-8-azabicyclo[3.2.1]-3β-acetic acid chloride

A solution of 7.3 g of the step d) compound in 60 ml $CHCl_3$ is treated with 4.4 ml thionyl chloride and refluxed 2 hours. The solution is then treated several times with toluene and evaporated to give the title compound.

f) 3-(6-Methoxyindolyl)- 8-benzyloxycarbonyl-8-azabicyclo[3.2.1]-3β-methyl ketone.

Methyl magnesium iodide, prepared from 1.6 ml methyl iodide and 630 mg magnesium in 80 ml ether, is treated at room temperature with 1.5 g 6-methoxyindole in 70 ml ether. The mixture is heated 2 hours under reflux, then cooled to 0° and treated with 3.2 g of the step e) compound in 50 ml toluene. The reaction mixture is stirred 2 hours, poured into 2N hydrochloric acid and extracted 3 times with $CH_2Cl_2$. The $CH_2Cl_2$-phases are washed with aqueous sodium bicarbonate solution and chromatographed on silicium dioxide eluting with ethyl acetete/hexane (1:10>1:1) to give the title compound as a colourless foam.

g) 3-(6-Hydroxyindolyl)-8-azabicyclo[3.2.1]-3β-methyl-ketone 300 mg of the step f) compound in 30 ml $CH_2Cl_2$ are treated at −78° with a solution of 0.8 ml boron tribromide in 10 ml $CH_2Cl_2$. After stirring 1 hour at −78° and 2½ hours at 0° aqueous sodium bicarbonate solution is added and the mixture extracted with n-butanol (3 times). The organic phases are evaporated and the residue is chromatographed on silica gel with $CH_2Cl_2/CH_3OH$/aq. $NH_3$ (95:5:1>85:15:1) to yield the compound as colourless crystals, m.p.>280°.

What we claim is:

1. A method of improving impaired approach oriented behavior in the treatment of stress-related manic-depressive disorders comprising administering to a subject in need of such treatment a therapeutically effective amount of a compound of formula Ia:

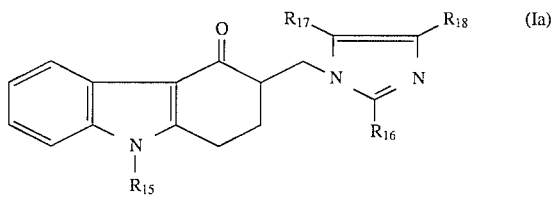

wherein $R_{15}$ is hydrogen, $(C_{1-10})$alkyl, $(C_{3-9})$cycloalkyl, $(C_{3-6})$alkenyl, phenyl or phenyl$(C_{1-3})$alkyl and one of the groups $R_{16}$, $R_{17}$ and $R_{18}$ is hydrogen, $(C_{1-6})$alkyl, $(C_{3-7})$cycloalkyl, $(C_{2-6})$alkenyl or phenyl$(C_{1-3})$alkyl, and the others independently are hydrogen or $(C_{1-4})$alkyl, which compound is in free base or pharmaceutically acceptable acid addition salt form.

2. A method according to claim 1 wherein the compound administered is 1,2,3,9-tetrahydro-9-methyl-3-[(2-methyl-1H-imidazol-1-yl)-methyl]-4H-carbazol-4-one, which compound is in free base or pharmaceutically acceptable acid addition salt form.

* * * * *